United States Patent [19]
Bierman et al.

[11] Patent Number: 5,314,411
[45] Date of Patent: May 24, 1994

[54] CATHETERIZATION SYSTEM WITH UNIVERSAL RETENTION DEVICE AND METHOD OF USE

[75] Inventors: Steven F. Bierman, 143 Eighth St., Del Mar, Calif. 92014; David C. Howson, Denver, Colo.

[73] Assignee: Steven F. Bierman, M.D., Del Mar, Calif.

[21] Appl. No.: 695,549

[22] Filed: May 3, 1991

Related U.S. Application Data

[63] Continuation-in-part of Ser. No. 518,964, May 4, 1990, Pat. No. 5,192,273, which is a continuation-in-part of Ser. No. 384,326, Jul. 24, 1989, abandoned.

[51] Int. Cl.⁵ ............................................... A61M 5/32
[52] U.S. Cl. .................................................... 604/174
[58] Field of Search ............... 604/180, 179, 178, 177, 604/175, 905, 174; 128/DIG. 22

[56] References Cited

U.S. PATENT DOCUMENTS

| | | |
|---|---|---|
| 747,360 | 12/1903 | Barry . |
| 2,525,398 | 10/1950 | Collins . |
| 2,533,961 | 12/1950 | Rouseau et al. . |
| 3,064,648 | 11/1962 | Bujan . |
| 3,167,072 | 1/1965 | Stone et al. . |
| 3,394,954 | 7/1968 | Sarns . |
| 3,686,896 | 8/1972 | Rutter . |
| 3,766,915 | 10/1973 | Rychlik . |
| 3,856,020 | 12/1974 | Kovac ............................ 604/177 X |
| 3,900,026 | 8/1975 | Wagner . |
| 3,906,946 | 9/1975 | Nordstrom . |
| 3,920,001 | 11/1975 | Edwards . |
| 3,973,565 | 8/1976 | Steer . |
| 4,037,599 | 7/1977 | Raulerson . |
| 4,082,094 | 4/1978 | Dailey . |
| 4,084,911 | 4/1978 | DeWitt . |
| 4,099,744 | 7/1978 | Kutnyak et al. . |
| 4,114,618 | 9/1978 | Vargas . |
| 4,116,196 | 9/1978 | Kaplan et al. . |
| 4,123,091 | 10/1978 | Cosentino et al. . |
| 4,129,128 | 12/1978 | McFarlane . |
| 4,133,312 | 1/1979 | Burd . |
| 4,161,177 | 7/1979 | Fuchs . |
| 4,224,937 | 9/1980 | Gordon . |
| 4,250,880 | 2/1981 | Gordon . |
| 4,316,461 | 2/1982 | Marais et al. . |
| 4,326,519 | 4/1982 | D'Alo et al. . |
| 4,362,156 | 12/1982 | Feller, Jr. et al. . |
| 4,392,853 | 7/1983 | Muto . |
| 4,405,163 | 9/1983 | Voges et al. . |
| 4,449,975 | 5/1984 | Perry . |
| 4,474,559 | 10/1984 | Steiger . |
| 4,516,968 | 5/1985 | Marshall et al. . |
| 4,585,435 | 4/1986 | Vaillancourt . |
| 4,711,636 | 12/1987 | Bierman . |
| 4,752,292 | 6/1988 | Lopez et al. . |
| 4,792,163 | 12/1988 | Kulle . |
| 4,838,858 | 6/1989 | Wortham et al. . |
| 4,863,432 | 9/1989 | Kvalo . |
| 4,880,412 | 11/1989 | Weiss . |
| 4,966,582 | 10/1990 | Sit et al. . |
| 4,981,469 | 1/1991 | Whitehouse et al. . |
| 4,997,421 | 3/1991 | Palsrok et al. . |
| 5,192,273 | 3/1993 | Bierman et al. ............... 604/905 X |

FOREIGN PATENT DOCUMENTS

| | | |
|---|---|---|
| 2341297 | 4/1975 | European Pat. Off. . |
| 114677 | 8/1984 | European Pat. Off. . |
| 169704 | 1/1986 | European Pat. Off. . |
| 0263789 | 9/1986 | Fed. Rep. of Germany . |
| 2063679 | 6/1981 | United Kingdom . |

Primary Examiner—John J. Wilson
Assistant Examiner—Jeffrey A. Smith
Attorney, Agent, or Firm—Knobbe, Martens, Olson & Bear

[57] ABSTRACT

A tubular adaptor releasably interconnects a conventional IV catheter hub to fluid supply tubing. A latching clip slidably mounted on the adaptor cooperates with flange portions on the catheter to secure the interconnection between the proximal end of the catheter and the adaptor. The adaptor is snapped into a base attached to the patient's skin by an adhesive pad. After the catheter connection is made, the adaptor, together with the clip, is rotated about 90° on the base into a low profile position, wherein the clip is close to the patient's skin.

28 Claims, 6 Drawing Sheets

CATHETERIZATION SYSTEM WITH UNIVERSAL RETENTION DEVICE AND METHOD OF USE

RELATED APPLICATION

This is a continuation-in-part of co-pending U.S. patent application Ser. No. 518,964, filed May 4, 1990, now U.S. Pat. No. 5,192,273, which is a continuation-in-part application of U.S. patent application Ser. No. 384,326, filed July 24, 1989, now abandoned.

BACKGROUND OF THE INVENTION

The present invention relates to a percutaneous catheterization system which is universally compatible with standard connectors, and, more particularly, to a system which facilitates the frequent replacement of the catheter tubing which is necessary in such catheterization procedures.

It is very common in the treatment of hospitalized patients to utilize intravenous (IV) catheters to introduce certain fluids directly into the bloodstream of the patient. Such procedures are also becoming more common outside of the hospital as the high cost of hospital medical care has brought about the advent of neighborhood out-patient clinics and home health care.

In IV catheterization, a supply of fluid is maintained in a container which is located at a height higher than the patient. The catheter tubing flows from the supply container to the location of introduction into the patient where it is attached to a catheter. This location is typically the back of the patient's hand or a vessel on the inside of the arm. Typically, a needle or other stylet is first introduced through the cannula portion of the catheter and into the skin of the patient at the desired location, and then removed after the cannula is inserted into the skin. The fluid then flows directly into the blood vessel of the patient by gravity, or, if necessary, by the pressure generated by the head of the fluid above the height of the patient.

In common practice, the catheter is maintained in place on the skin of the patient by the use of adhesive or surgical tape. Likewise, the connection between the tubing and the catheter is also maintained by use of tape. In addition, a safety loop is typically formed in the tubing so that any tension applied to the tubing is not passed directly to the cannula of the catheter but is taken up in the slack of the safety loop. This loop is also typically taped loosely to the skin of the patient. This entire taping procedure takes several minutes of the valuable time of health practitioners performing this procedure.

IV catheterization is frequently maintained for several days, depending upon the condition of the patient. This longevity requirement gives rise to several problems associated with IV catheters. For example, the catheter tubing is generally replaced every 24 to 48 hours in order to maintain the sterility of the fluid and the free-flow of the fluid through the tubing. Thus, a health practitioner is often called upon to frequently change the tubing and to retape the connection. Furthermore, the taping of the catheter to the skin of the patient often covers the location of insertion of the cannula. Thus, the tape must be removed in order to inspect the insertion location for inflammation or infection and a complete taping procedure again be initiated. In short, a great deal of valuable time of the health practitioner is used in applying significant amounts of surgical tape to IV catheters. Further, the frequent application and removal of surgical tape often results in the excoriation of the skin of the patient in the area of the insertion.

A number of catheterization systems have recently been developed which improve the stabilization of the catheter system and/or obviate the need for frequent application and removal of surgical tape during IV tubing changes. One such system is shown in U.S. Pat. No. 4,250,880, wherein a disposable catheter stabilizing fitting comprising a catheter hub-retaining cradle is attached to a laminar base, the base having an adhesive undersurface for attachment to the patient. The cradle is designed to hold the catheter hub at a suitable angle to avoid bending or crimping of the catheter so as to facilitate access to the point of catheter insertion to the skin, however, the device is still required to be secured and stabilized by being overlaid with adhesive tape.

Another catheterization system is described in U.S. Pat. No. 4,711,636, comprising a specially designed cannula which is attachable via an adaptor to an IV tubing. The cannula is removably attached to a base, which is adhesively attachable to the skin of a patient. The cannula is adapted to be secured to the base portion in a snap-fit engagement so as to obviate the necessity for the time consuming application of surgical tape or other apparatus to stabilize the catheter, as previously mentioned. However, this cannula is specially adapted for attachment to the base portion of the assembly, and therefore, cannot be used with conventional luer-type connectors on conventional cannula apparatus.

The above-referenced pending parent patent application discloses a system which represents an improvement over the apparatus shown in above-mentioned U.S. Pat. No. 4,711,636 in that the system in the pending application can be used with conventional luer-type connectors on conventional cannula apparatus. However, one of the difficulties of utilizing an adaptor which can attach to conventional connectors is that there are some dimensional variances in conventional connectors. Typically, such connectors employ a tapered hub with an outwardly extending flange on the larger end. That pending application employs a retention latch which is manually movable to latch onto the flange on the end of the connector, and thus securely hold the connector with respect to the adaptor. This works quite well with most standard-type connectors, but connectors having slight dimensional variations do not fit so well because there is no means in the latch to accommodate such variations. Thus, a need exists for a latch that can handle such variations.

The manually operated mechanism for opening the latch in the above-referenced application and in the above-mentioned U.S. Pat. No. 4,711,636 extends outwardly away from the patient skin to facilitate operation. While the device is relatively small, it does extend outwardly enough such that it can interfere in taping or other medical procedures, or can interfere with patient movement. Thus it is desirable that a system be provided which improves that aspect.

Another type of standard IV connection involves the use of "injection sites." Although such sites may occur at various locations in IV catheterization systems, one common location is where the catheter is directly inserted into the patient's vein. This injection site connection comprises a cylindrical tube mounted on the end of the catheter with a rubber septum or "buff cap" stretched over or inserted within the open end of the tube. Originally, this type of connection was intended to facilitate manual injections. That is, the nurse can insert a needle through the rubber material of the septum and into the lumen on the other side thereof in order to cause medication to enter the patient. Once the needle is withdrawn, the rubber material of the septum closes the puncture area and seals the lumen. In addition to manual injections, however, this type of septum connector can be left in place in order to permit secondary attachments for IV purposes. The top surface of the septum can be easily cleaned and sterilized with an alcohol-saturated pad. Thus, this type of septum or buff cap connection is an alternative to a catheterization system utilizing a luer lock or hub on the end of the catheter. In the IV context, the septum connection is made up only by the insertion of a needle attached to the end of the IV line which is inserted through the rubber material of the septum.

However, along with the convenience provided by this septum-type connection, a number of problems have also arisen. First, the mechanical security of the connection of a needle inserted through rubber is obviously very poor. This problem is particularly aggravated by the duration of the connection. With the advent of long-term infusion, which has replaced manual injections for many applications, the needle/septum connection remains in use for many hours or days. Furthermore, this type of connection is frequently used in the home healthcare context. Because the patient is often ambulatory, the connection frequently disengages. As a consequence, nurses typically try to tape the connection together. However, this procedure takes extra time and does not protect the connection site from contamination. Also, with more frequent use of IV therapy, nurses are exposed many times each day to sharp needles. This type of septum connection increases the risk of accidental self-injection. Because many of the drugs contained in the IV solution are potent and toxic, this may be a very significant risk to a nurse using a septum connection.

Previous devices have not adequately addressed these problems. Most manufacturers have provided two customized adapters in order to avoid the above problems presented by the septum connection. For example, one component would comprise a special device incorporating the rubber cap and a second customized device incorporates the IV needle. Thus, standard septum connectors cannot be utilized. Furthermore, connector components are not interchangeable with other manufactured components. This two-piece customized approach also increases the expense associated with this form of IV therapy. Furthermore, previous devices do not provide adequate protection against accidental self-injection. The customized components are often bulky and prevent injections close to the patient's skin. Furthermore, these devices do not provide prevention against contamination of the septum surface after the connection is made. In other words, nurses still find it necessary to tape the connection, increasing the expense and time consumption of this procedure.

SUMMARY OF THE INVENTION

Briefly stated, the invention employs an adaptor having a tubular portion with a forward end compatible with either a standard luer-type connector or a septum-type connector; and a clip slidably mounted on the adaptor to latch the connector to the adaptor. The clip includes a forward latch portion which cooperates with a flange on the rear of the connector to secure the connector to the adaptor. Because the clip is slidable, it can accommodate variations in the axial position of the connector flange or septum configuration. Preferably, the latch has a somewhat flexible forked tip that straddles the end of the connector, and accommodates variations in connector diameters.

In one embodiment, the adapter body is provided with a forward end adapted to be inserted within the end of a standard luer-type connector. In another embodiment, the invention utilizes an IV needle mounted within and protruding from the forward end of the tubular portion of the adapter so as to be compatible with a standard septum-type connector. This embodiment also utilizes a shield which substantially prevents the risk of accidental self-injection and reduces the risk of contamination of the septum during connection. In both embodiments, the adapter is streamlined and lightweight in order to avoid discomfort and bulkiness, and to permit intricate injections close to the patient's body. Furthermore, the adapter can be rotated to a low-profile position, in order to enhance the security of the connection. Thus, as an important advantage of this invention, the adapter is compatible with a wide range of standard IV connectors, and the need for special or customized components is eliminated.

In a preferred form of the invention, the clip is mounted on the adaptor by means of an elongated plate-like ratchet element which extends parallel to the adaptor tubular portion. The element is mounted on the end of an arm that extends radially outwardly from the adaptor tubular portion. The clip is slidably mounted on this plate-like ratchet element. Depressing the rear of this element, with the clip mounted thereon, toward the adaptor tubular portion allows it to pivot about the arm so as to move the forward end of the ratchet element, together with the forked end of the clip, radially outwardly to permit engagement and disengagement of the connector to the end of the adaptor. Withdrawing the depressing force allows the forked end of the clip to return inwardly to its normal latching position.

The clip and the ratchet element include ratchet teeth and an interengaging pawl for maintaining those parts in a manually selected position. In a preferred form of the invention, the ratchet teeth are formed on the radially outer surface of the ratchet element and a tongue-like, resiliently mounted pawl formed on the clip cooperates with these teeth.

The apparatus also includes a base which is adapted to be attached to the patient's skin by means of an adhesive pad. The base can be formed integral with the pad or selectively detachable therefrom. The base has a pair of upstanding legs which define a space for receiving the adaptor and are constructed to flex outwardly at the upper end to provide a snap fit with the adaptor. Preferably, this snap fit includes an inwardly extending detent on the upper end of each leg. The detents fit within an annular groove formed on the outer surface of the adaptor tubular portion. The detents hold the adaptor to the base and permit the adaptor to rotate from its upright position, when the connection is being made to the connector on the end of a catheter, into a lower profile "stored" position closer to the base and the patient's skin. In this position the components are less likely to interfere with other surrounding actions.

DETAILED DESCRIPTION OF A PREFERRED EMBODIMENT

Figure 1:
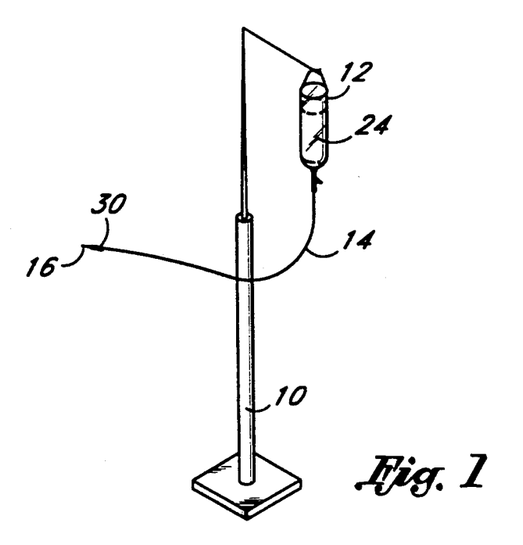
FIG. 1 is a perspective, schematic view of a typical catheterization installation using the catheter adaptor of the present invention.

Referring now to FIG. 1 there is shown a basic set-up for a catheterization procedure, including a support stand 10, a container 12, a length of IV tubing 14 connected by an adaptor 30 to the actual catheter 16, which is inserted into the patient. Typically, a patient is lying in a bed or is seated adjacent to a stand 10. Fluid 24, to be dispensed into the patient, is maintained in the container 12 and is fed under the pressure of the head of the fluid above the patient, through the IV tubing 14 and catheter 16 into the patient.

ADAPTER FOR LUER-TYPE CONNECTION

The embodiment of the present invention adapted to be compatible with the standard luer-type connections will first be described in relation to FIGS. 2–4a. However, it should be pointed out that the principles of the present invention are not limited to either luer- or septum-type connections, but can be utilized with a wide variety of IV connectors, both presently existing and hereinafter arising.

Figure 2:
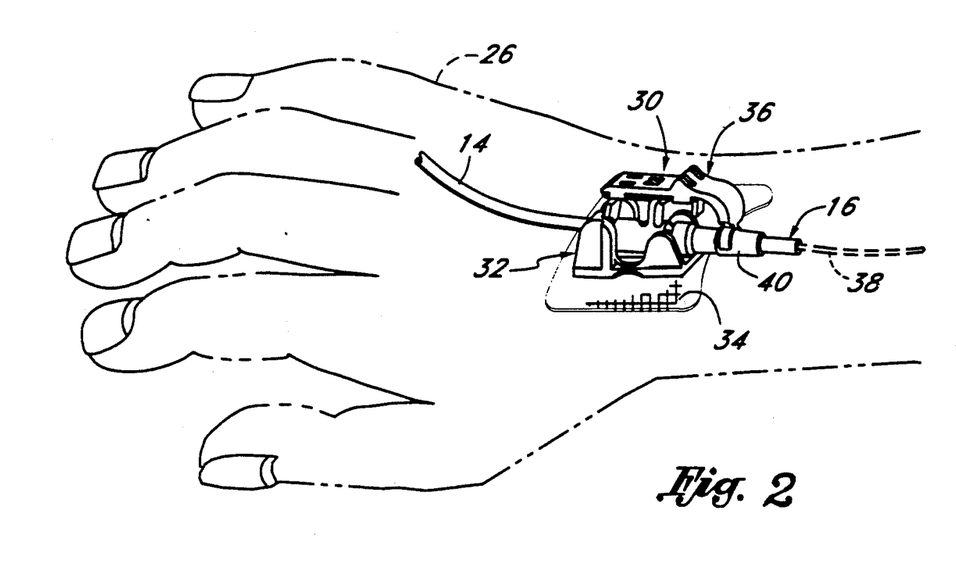
FIG. 2 is a perspective view of catheterization apparatus of the present invention, mounted on the back of a patient's hand.
Figure 3:
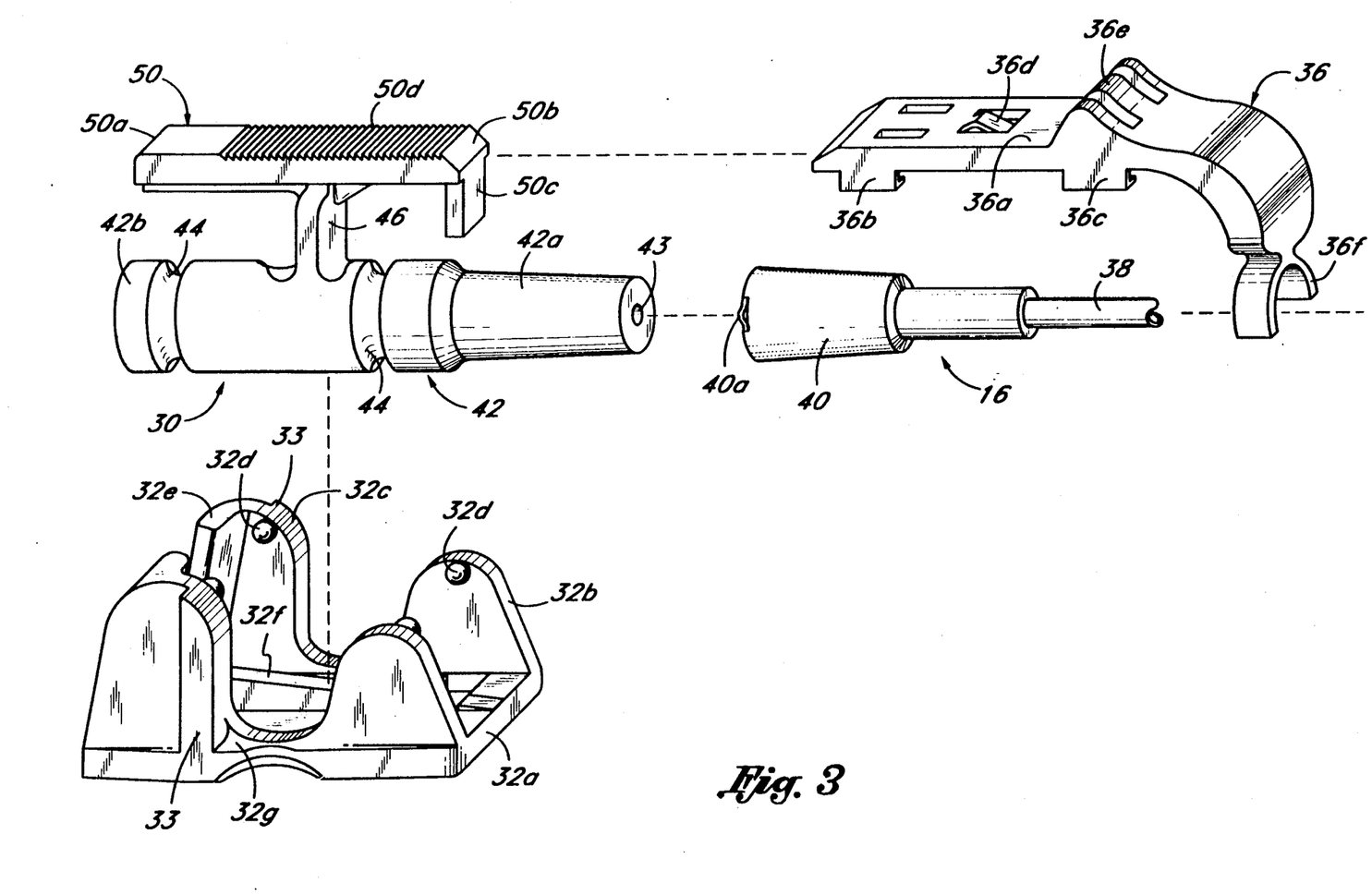
FIG. 3 is an exploded perspective view of the apparatus of FIG. 2.

FIG. 2 illustrates an enlargement of the catheterization apparatus of the present invention, positioned in the back of a patient's hand 26, shown in phantom lines. As better seen in FIGS. 3 and 4, the apparatus includes the adaptor 30 interconnecting the catheter 16 and the tubing 14, a base support 32 mounted on a pad 34, and a latching clip 36. For convenience, the pad 34 upon which the base support 32 is integrally mounted is shown only in FIG. 2. Such pad 34 could be integral with the base 32 or selectively detachable therefrom. The base can be integrally mounted on the pad 34 in any one of various ways well known in the art, such as adhesive. In the detachable mode, velcro or other well-known means can be used to mount the base on the pad. Furthermore, for clarity of illustration and description, FIG. 3 illustrates the latching clip 36 in exploded fashion from the adapter 30; however, it should be understood that, in use, these two elements are initially mated together.

The catheter 16 includes a cannula 38 and a conventional hub 40, having a frusto-conical shape and terminating at its rear end in radially outwardly extending flange portions 40a. Some hubs have a continuous flange.

The adaptor 30 includes a main elongated tubular body 42 having a passage 43 therethrough. The body has a forward end 42a which tapers to fit within an opening in the catheter hub 40. The rear end 42b of the tubular body 42 is adapted to receive the downstream end of the tubing 14. The adaptor further includes a pair of axially spaced annular grooves 44 formed on the exterior of the tubular body. Extending outwardly from the body 42 in cantilever fashion is a support arm 46. Positioned on the radially outer end of the arm 46 is a ratchet element 50 that extends generally parallel to and spaced from the axis of the tubular body 42. The connection to the support arm 46 is between the ends of the ratchet element 50. The adaptor body 42, the arm 46 and the ratchet element 50 are preferably formed as one piece, preferably of a stiff but somewhat flexible plastic. Thus, although the arm 46 and the element 50 are stiff, the element can pivot somewhat about the upper end of the arm, and the arm can flex somewhat about its lower end. Thus depressing the rear end 50a of the ratchet element 50 towards the body 42, will correspondingly move the forward end 50b away from the body 42.

Formed integral with the forward end 50b is a depending stop 50c, which extends toward the body 42 and limits the movement of the forward end 50b towards the tubular body, and prevents fatigue of flexing of the arm 46 and element 50. Formed on the upper or radially outer, flat surface of the ratchet element 50 are a series of ratchet teeth 50d which extend laterally generally parallel to the axis of the tubular body.

The anchor pad 34 is preferably made of a woven cloth material having a self-adhesive backing for attachment to the skin; or alternatively, a foam material with adhesive back. The anchor pad may also be connected to a support for a loop of tubing, and the pad may be specially formed for a left hand or a right hand mounting.

The adaptor base 32 has a generally rectangular lower wall 32a, having its lower surface suitably attached to the top surface of the anchor pad. A pair of spaced upstanding legs 32b are located on the forward end of the base, and a second pair of outwardly extending legs 32c are mounted on the rear portion of the lower wall 32a. These legs define a space sized to receive the tubular body of the adaptor 30. Each leg has on its upper end an inwardly extending detent or nib 32d. The spacing between detents in each pair of legs is slightly less than the smaller diameter of the grooves 44 on the adaptor. Also, the detents 32d on the legs 32b are spaced upwardly from the bottom wall 32a a distance greater than the radius of the adaptor tubular body, and the detents 32d on the legs 32c are spaced above a rib 32f.

The base is made of relatively stiff plastic material but is somewhat flexible, such that the upper ends of the legs, which are supported in cantilever fashion from the base wall 32, can be forced outwardly by the adaptor when it is placed between the legs. When the adaptor is seated, the upper ends of the legs snap inwardly to their original position, such that the adaptor is securely held within the base. Since the detents 32d are positioned within the annular grooves 44, the adaptor is also securely positioned in its axial direction. The base also includes a rear upstanding wall 32e, which further helps position the adaptor within the base. The base rib 32f is positioned between the legs 32c and extends upwardly to support the adaptor. The upper edge of the rib is angled so that it is higher towards the rear of the base than it is towards the forward portion, with the result that the adaptor is positioned at a desired angle. A horizontal ledge 32h (FIG. 4) can be provided on the interior side of the rear wall 42c at the rib height to further support the adaptor in its angled position.

The base 32 includes a waist area 32g on the bottom wall 32a between the front and rear legs. This area extends inwardly from the sides of wall 32a and slightly beneath the adaptor to facilitate gripping the adaptor with a thumb and forefinger.

The clip 36 has a main portion 36a with a generally flat rectangular shape. The clip has positioned on its side edges a forward pair of depending, retainer lugs 36c and a rear pair of depending retainer lugs 36b. These lugs include inwardly extending portions which in cooperation with the lower surface of the main portion 36a define side spaces to receive the ratchet element 50 on the adaptor.

Figure 4:
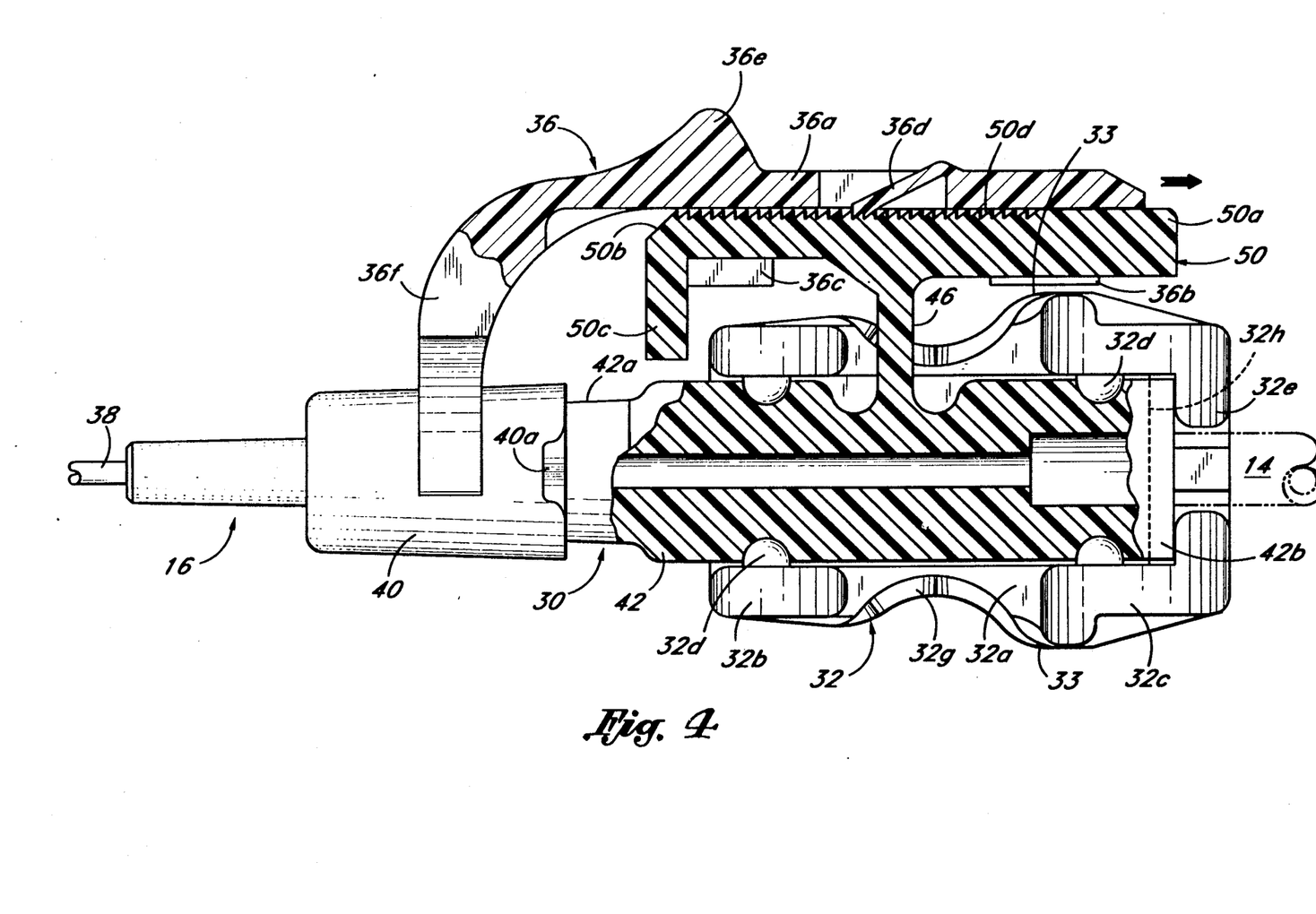
FIG. 4 is a top, partially sectionalized view of the apparatus of FIG. 3, illustrating the operation of the resiliently-mounted movable clip and ratchet arrangement, and also illustrating the rotation of the adapter to its low-profile or "stored" position.

Centrally positioned on the clip is a tongue or pawl 36d supported in cantilever fashion from the main body 36a of the clip. The rear portion of the pawl is formed integral with the body 36a, and the forward end is free and depends downwardly below the lower surface of the body 36a, as best seen in FIG. 4. The lower edge of the pawl is a straight line and is adapted to cooperate with the ratchet teeth 50d on the ratchet element 50 of the adaptor.

Positioned slightly forwardly from the tongue is an upwardly extending bump 36e adapted to be engaged by a person's finger or thumb so as to slide the clip 36 on the ratchet element 50. The forward end of the clip curves downwardly and includes a fork-shaped latch 36f adapted to straddle the hub of the catheter. The latch preferably has a curved circular shape that extends more than 180°, such as 190° to 200°. This horseshoe shape enables the latch to slip onto a tapered hub but yet lightly grip it and enables the latch to accommodate a variety of hub shapes and surfaces.

In use, the catheter 16 is installed in conventional fashion. That is, a needle is inserted into the patient's blood vessel; and while holding the needle still, the conventional catheter 16 is slid over the needle and into position within the vessel. The needle is then carefully withdrawn leaving the catheter in position. The forward end 42a of the adaptor 30 is inserted into the catheter hub 40. In accordance with the invention, the clip 36 which has been slidably mounted on the adaptor ratchet element 50 is in a forward position so that it does not interfere with the insertion of the adaptor into the catheter hub. On the other hand, if the clip 36 (and more particularly the forked latch 36f) impedes the interengagement of the hub 40 and the forward end 42a of the adapter 30, the forked latch 36f can be easily removed from the alignment area by depressing the rear end 50a of the ratchet element 50. One of the advantages of the present invention is that this action of operating the latch to facilitate the catheter connection can be easily performed with one hand, while the other hand holds the catheter. Whether or not the latch needs to be manipulated, once the hub 40 is engaged on the adapter forward end 42a, the clip 36 is then slid rearwardly causing its forked latch 36f to engage the forward surface of the flange portion 40a on the catheter hub, thereby securely attaching the adaptor to the catheter.

Because conventional catheter hubs have dimensional variations, it is desirable that the clip be adjustable to accommodate the various sizes and yet securely hold the adaptor and the catheter hub together. The clip 36 is easily movable rearwardly on the ratchet element, and the ratchet teeth cooperate with the clip tongue to resist forward movement and hold the clip in the manually selected position.

The adaptor is then snapped into the base 32. In doing this, the adaptor is pressed between the upstanding legs of the base with the detents on the adaptor legs sliding within the annular groove to hold the adaptor in the base. The anchor pad 34 attached to the adaptor base is then positioned in the desired location adjacent to the puncture point in the patient's skin. As noted above, the adaptor and the upper end of the centrally located rib 32f and the ledge 32h in the base causes the forward end of the adaptor to be angled downwardly to be best aligned with the axis of the catheter hub.

To reduce the profile of the clip and the adaptor mounting arm, the adaptor together with the clip can be rotated about 90°, in either direction, to the low profile or "stored" position shown in FIG. 4. In other words, FIG. 4 is a top plan view similar to FIG. 2 except that the latching clip 36 is shown in a rotated position. In this position, the adaptor mounting arm extends between the front base legs 32b and the rear base legs 32c, such that the arm is close to the adaptor base, generally parallel to the patient's skin. The height of the assembly has been reduced to the height of the base 32 and thereby reducing the risk of the assembly interfering with surrounding actions. Once so positioned, the adaptor will normally remain in this position.

Figure 4A:
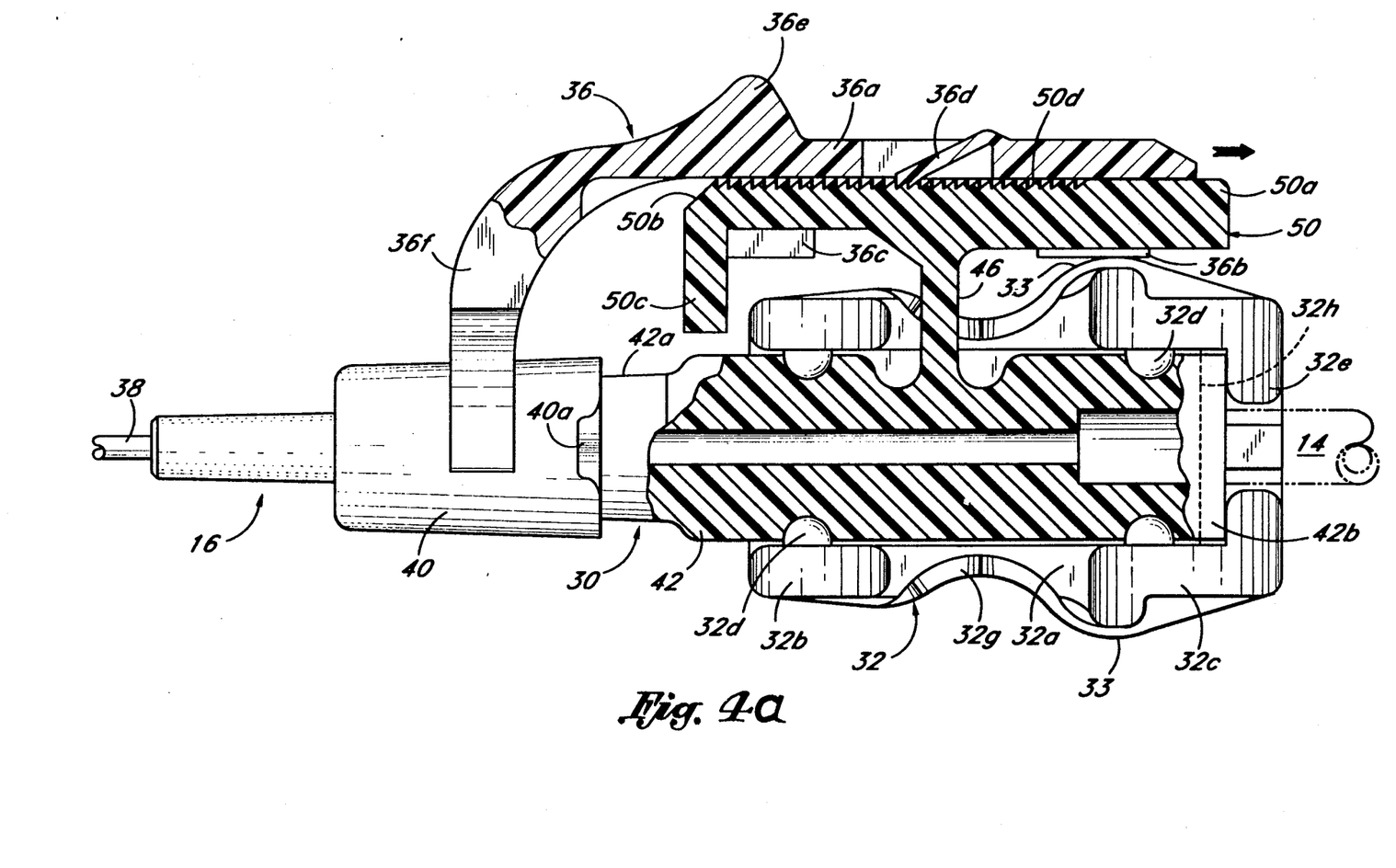
FIG. 4a is an alternate embodiment of the adapter of FIG. 4, illustrating a retention device for securing the adapter in its rotated or stored position.

In order to ensure that this position is maintained, the retention device illustrated in FIG. 4a can be utilized. In this embodiment, the retainer lugs 36b on the clip 36 can be extended so that they engage, in press fit relation, a rib 33 (shown in FIG. 3) formed on the legs 32c of the base 32. A similar engagement (not shown) could be utilized by extending retainer lugs 36c so that they engage a similar rib (not shown) formed on the exterior surface of legs 32b. This press fit interconnection causes the adapter body 42, and more particularly the annular grooves 44, to be held more tightly in relation to the detents 32d. Thus, the adapter is securely retained in its rotated or "stored" position until the adapter and its associated tubing is to be removed and replaced. At that time, the press fit or frictional engagement holding the clip 36 in the stored position can be easily overcome by manual manipulation in order to rotate the adapter to its initial position, shown in FIG. 2.

In replacing an adaptor and tubing, the procedure is essentially reversed from that set forth above, except that the catheter remains in the patient and the adaptor base remains as positioned. Leaving the catheter in position, of course, minimizes discomfort to the patient, and allowing the adaptor base to remain eliminates irritation to the patient's skin that would be caused by removal and replacement. Also operator time is thus saved during such replacement. In removing the adaptor from the base, the attendant's forefingers and thumb can be placed in the base waist area, also engaging the adaptor. The adaptor is then snapped out of the base with a pinching action. The adaptor is separated from the catheter by depressing the rear of the clip and the clip support element to raise the latch so that the adaptor can be withdrawn rearwardly from the catheter.

ADAPTER FOR SEPTUM-TYPE CONNECTOR

Figure 5:
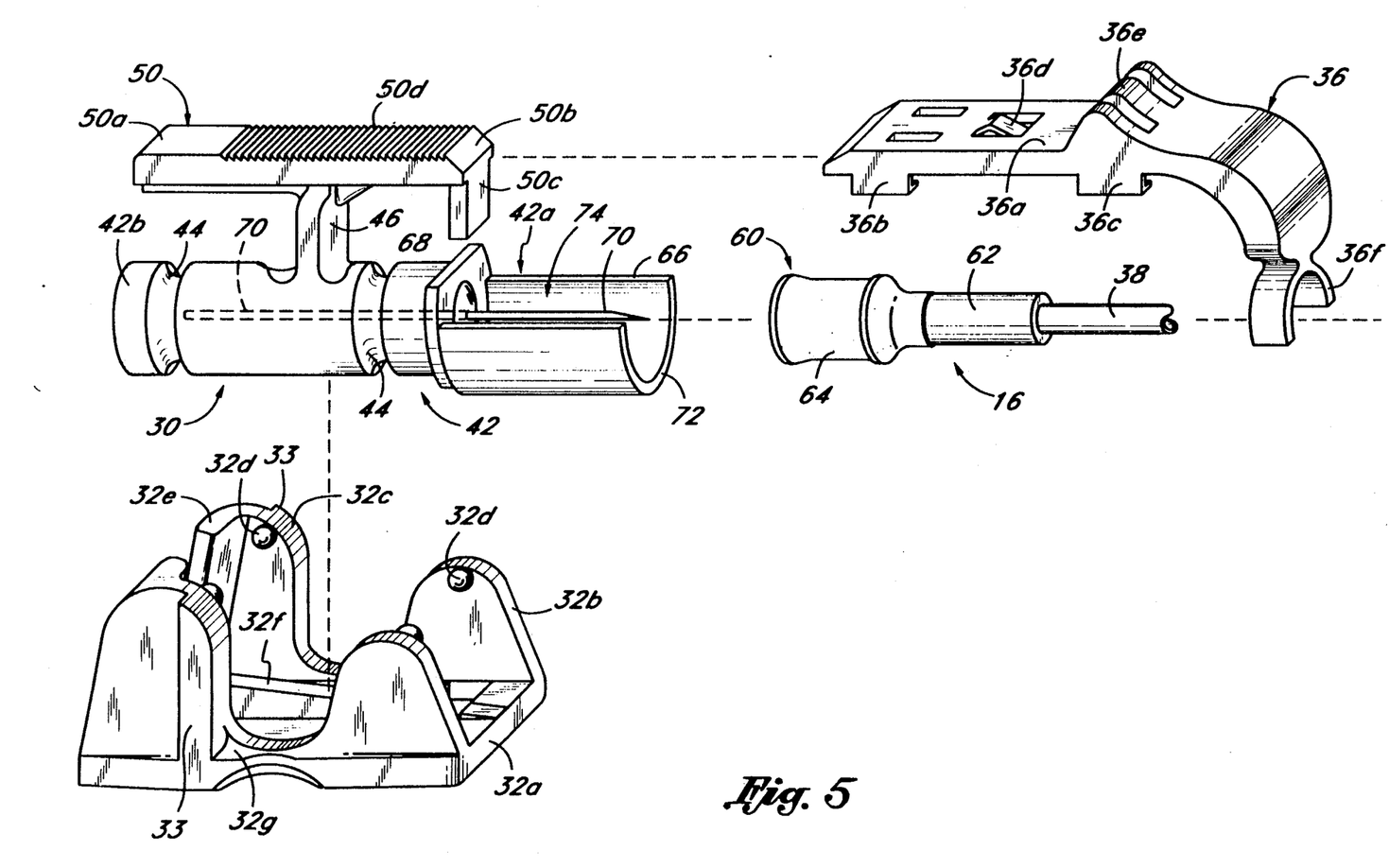
FIG. 5 is a perspective view similar to FIG. 3, illustrating the embodiment of the present invention which is compatible with a standard septum-type connector.

Another embodiment of the present invention comprises an IV adapter which is compatible with standard septum-type connectors. In this context, it is common for a septum-type connection to be utilized in combination with a basic IV catheterization system, as illustrated in FIGS. 1 and 2, except that the luer-type connector 40 illustrated in FIG. 2, mounted on the end of the catheter or cannula 38, is replaced by a septum-type connector 60, as illustrated in FIG. 5. This type of connector comprises a cylindrical tube 62, typically constructed from plastic, mounted on the end of the cannula 38, which, in turn, inserts into the vein of the patient. The end of the cylindrical tube 62 is provided by a rubber septum or cap 64 (also referred to as a "buff cop") which is stretched tightly over the end in order to completely close the opening or lumen thereof. Thus, the cap 64 can be perforated by an injection needle in order to administer medication to the patient. When the needle is removed, the rubber material of the cap 64 self-seals in order to prevent leakage.

In use, the septum-type connector is often referred to as a "heparin lock." In order to prevent blood from clotting at the catheter tip, the connector is frequently filled with heparin, which is an anti-coagulant. When the needle is disconnected from the cap, the connector is said to be "locked," i.e., there is no flow.

The adapter 30 of FIG. 5 advantageously provides a secure connection with these and similar types of heparin locks or septum-type connectors. For ease of illustration and description, the adapter 30 of FIG. 5, like FIG. 3, illustrates the clip 36 in exploded relation to the ratchet element 50. However, it will be understood that, in use, prior to connection with the catheter 16, the adapter 30 includes the clip 36 in mated relation to the ratchet element 50 (and typically detached from the base 32).

The adapter 30 of FIG. 5 is similar to the adapter of FIG. 3, and a description of like elements, indicated by identical reference numerals, will not be repeated; rather, features peculiar to this embodiment shall be described below.

Referring then to FIG. 5, the adapter 30 comprises a body 42 having a forward end 42a having a shield 66. The shield mounts on a planar flange 68 which in turn mounts on the end of the tubular body 42 of the adapter 30. It will also be noted that the stop device 50c engages the top of the flange 68 so as to prevent over extension or fatigue of the arm 46. As shown in FIG. 5, the shield 66 is partially circular or cylindrical in shape, and extends longitudinally in front of the body 42. Running longitudinally through the body 42 and mounted therein, as shown in dotted lines, is an IV needle 70. The end of an IV tubing (not shown) is then connected to the rear end 42b of the adapter 30 so that fluid is in communication with the IV needle 70. The needle 70 also extends beyond the end of the body 42 and is approximately coaxial with the axis of the shield 66.

Preferably, the distal end 72 of the shield 66 extends slightly beyond the tip of the needle, and the sides of the shield extend above the axis of the needle so as to substantially partially surround the needle. Preferably, the shield 66 circumscribes approximately 180°; however, a circumference of a wide range (such as 160°-220°) would also be within the scope of the invention.

This configuration of the needle 70 and shield 66 shown in FIG. 5 provides a high degree of protection from accidental self-injection. The shield provides such protection on substantially three sides of the needle. The only side that is left open is the upper side 74, which advantageously permits improved vision for the user as the adapter 30 is guided into a connection relationship with the cap 64 of the septum. In addition, the shield 66 serves as a guide for those users whose eyesight may not be ideal. Furthermore, the open upper surface 74 of the shield permits the clip 36 to engage the septum, as explained below in more detail. Upon engagement, the shield protects the septum and inhibits contamination. Advantageously, the present invention holds the connection substantially parallel to the skin.

The clip 36 of the adapter 30 serves to securely retain the interconnection between the needle and the septum in a manner similar to that described above in FIGS. 2-4. Initially, the adapter 30 is typically disengaged from the base 32. The clip 36, although mated with the ratchet element 50, is extended distally therefrom in order to prevent any interference with the septum connection. Because the cap 64 of the septum typically exhibits a larger diameter than standard luer locks or other types of connectors, it may be necessary to elevate the latch 36f in order to avoid interference. This can be done, as described above, by simply depressing the rear end 50a of the ratchet element 50 in order to allow the septum to engage the needle.

It will also be noted in FIG. 5 that there is sufficient clearance between the body 42 of the adapter 30 and the rear end 50a of the ratchet element 50 in order to permit the latch 36f to be substantially elevated. Once the septum connection is joined, the clip can be slidably moved toward the rear of the adapter 30 until the latch 36f engages a circumferential portion of the cap, thereby securely retaining the septum connection in its desired position. This secure connection is maintained by the interengagement of the pawl arm 36d and the ratchet members 50d, in a manner described in connection with FIG. 4 above. When disconnection is desired, the clip 36 is simply depressed in order to disengage the latch 36f from the septum cap 64. The adapter 30 can then be pulled toward the rear in order to cause the needle 70 to disengage the cap.

It should be noted that, not only is the adapter 30 of the present invention compatible with a variety of IV connectors, it is also compatible with connectors having various diameters and configurations (i.e., unique connectors). Thus, the present invention reduces the cost of typical IV catheterization and facilitates the interchangeability of components.

Figure 5A:
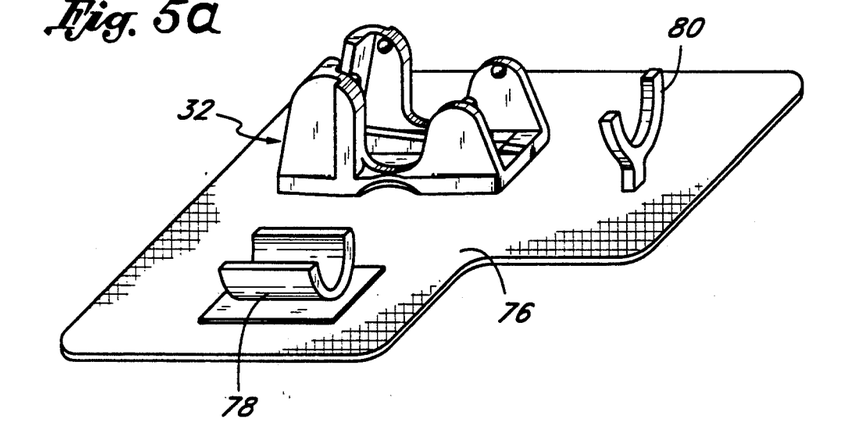
FIG. 5a illustrates an anchor pad which optionally can be used in combination with the connector of FIG. 5 to secure the septum connection to the skin of the patient.

FIG. 5a illustrates an anchor pad 76 which can be optionally utilized with the adapter of FIG. 5. Like the anchor pad 34 of FIG. 2, the anchor pad 76 illustrated in FIG. 5a comprises a base 32 upon which the adapter 30 can be mounted for rotation and retention in a manner similar to that described above. The pad also includes a tubing clip 78 into which a safety loop formed in the IV tubing can be inserted. Forward of the base 32 is a clip 80 in order to retain the cylindrical element 62 of the septum connector 60 (shown in FIG. 5). This clip 80 is preferably manufactured from a resilient material, and is thin and flexible in order to retain the cylindrical tube 62 while still permitting slight movement thereof. This combination prevents pain and discomfort to a patient.

Figure 6:
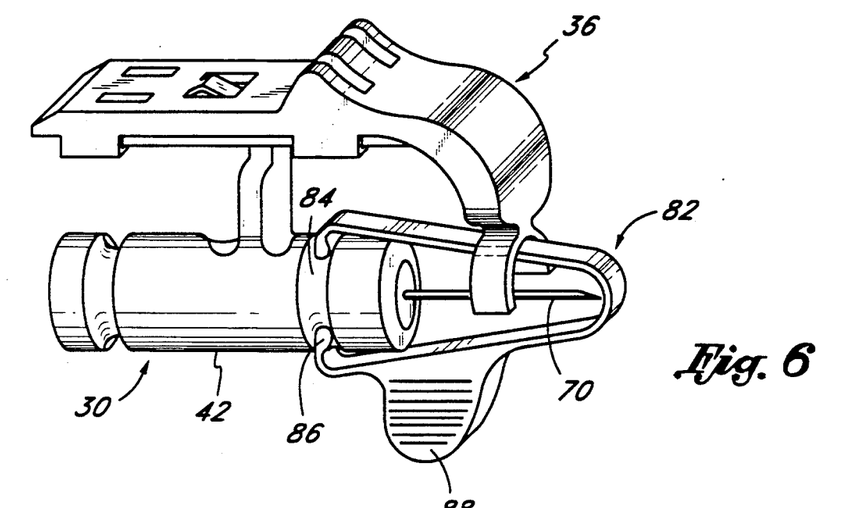
FIGS. 6 and 6a illustrate another embodiment of the septum connector of FIG. 5, illustrating a removable needle cap to prevent accidental self-injection.
Figure 6A:
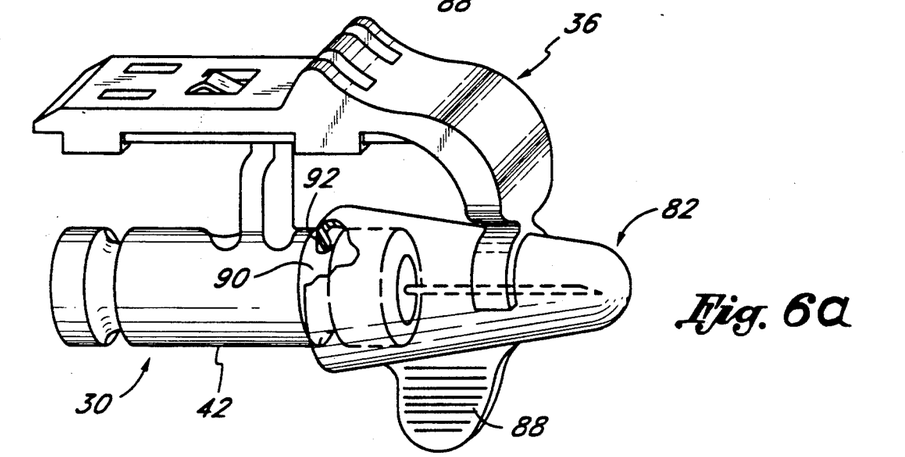

FIGS. 6 and 6a illustrate an alternate embodiment of an adaptor 30 utilizing a needle cap 82 to prevent accidental self-injection. In this embodiment, the forward end of the body 42 of the adaptor 30 is provided with a pair of substantially parallel grooves 84 formed on the upper and lower sides of the body 42. Mating with the grooves are edges 86 of the needle cap 82. The needle cap is substantially U-shaped in cross-section and rotated approximately 90°, so that when engaged on the end of the adaptor 30, the cap surrounds the needle 70 on two or three sides. Only one side of the cap needs to be left open in order to permit the cap 82 to be slidably engaged in the grooves 84. This cap prevents accidental self-injection when the adaptor is disengaged from the septum-type connector. The cap also includes a lower finger grip 88 to facilitate decapping and recapping, while permitting the fingers to avoid the sharp tip of the needle 70.

In another arrangement, shown in FIG. 6a, the needle cap 82 can completely enclose the needle 70 on all sides and be engageable on an annular groove 90 formed on the forward end 42a of the adaptor 30 by means of a press-fit or interference fit with an annular lip 92. Alternatively, the press fit engagement of the cap 82 can be made with the annular groove 44 (FIG. 5).

While a preferred arrangement of the catheter mounting apparatus has been illustrated and described, it should be understood that various changes and modifications to the apparatus will readily come to mind and fall within the scope of the invention as set forth in the appended claims.

We claim:

1. An apparatus for removably connecting together a fluid supply tube and an intravenous catheter, said apparatus comprising:
an adaptor having a tubular body with a passage extending through said body, the body having a forward end comprising a needle to engage a septum connector disposed on the catheter end, and a rear end adapted to be connected to the tubing; and
a clip slidably mounted on said adaptor for movement in a direction generally parallel to an axis through said passage, said clip including a latch adapted to cooperate with said catheter end to hold the catheter end on said forward end, said clip and said adaptor having an interengaging element to hold said latch in a manually selected position on said adaptor.

2. The apparatus of claim 1, wherein said adaptor additionally comprises a support arm extending outwardly from said adaptor body and a clip support element mounted on said arm, said clip is slidably mounted on said clip support element.

3. The apparatus of claim 2, wherein said interengaging element includes a plurality of ratchet teeth positioned on said clip support element, and a pawl positioned on said clip and flexibly biased against and slidable over said teeth, said pawl cooperating with said teeth to hold said clip in said selected position.

4. The apparatus of claim 2, wherein said clip support element has a generally flat elongated shape and said clip comprises lugs which cooperate with edges of said clip support element to guide the movement of said clip on said clip support element.

5. The apparatus of claim 4, wherein said lugs are positioned on edges of said clip and slidably fit under the edges of said clip support element.

6. The apparatus of claim 5, wherein said interengaging element includes a plurality of ratchet teeth on an upper surface of said clip support element, and said clip has a flexibly mounted pawl which cooperates with said teeth to hold the clip in said selected position.

7. The apparatus of claim 2, wherein said clip support element and said support arm are constructed in a manner to enable said clip support element, together with said clip, to be manually pivotable to move said latch away from said forward end of said adaptor so as to permit connection and disconnection between the septum connector and said forward end.

8. The apparatus of claim 7, wherein said clip support element generally has an elongated shape symmetrically connected on the outer end of said support arm, the connection between said support arm and said clip support element permitting pivoting movement of said clip support element in a manner such that depressing a rear end of said clip support element moves a forward end of said clip support element away from said adaptor body.

9. The apparatus of claim 8, wherein said clip support element includes a depending stop formed on the forward end of the clip support element, the stop being located to limit the movement of the forward end of said clip support element towards said tubular body.

10. The apparatus of claim 1, additionally comprising an elongated, generally semi-circular shield disposed about said needle proximate to said forward end to prevent unintentional engagement of said needle with other objects.

11. The apparatus of claim 1, additionally comprising a needle clip removably covering said needle to prevent accidental self-injection, said needle clip having a generally semi-circular body formed by the rotation of a U-shaped cross section through approximately 90°, and at least two edges at an open end of said needle clip, said adapter body comprising at least two grooves disposed about said forward end and adapted to engage said needle clip edges to removably secure said needle clip to said adapter body.

12. The apparatus of claim 11, wherein said needle clip edges form an annular flange circumscribing said open end and said adapter body grooves form an annular groove positioned to mate with said needle clip annular flange.

13. The apparatus of claim 5, wherein said interengaging element includes ratchet teeth and a pawl adapted to cooperate with said teeth to hold said clip in said selected position.

14. The apparatus of claim 1, including a base adapted to be mounted on a patient and to support said adaptor, said base and said adaptor having structure providing a releasable snap-fit engagement that permits said adaptor to be moved about an axis through said body from an operative position wherein said arm extends outwardly on a side remote from said base to a stored position wherein said arm is located close to said base.

15. The apparatus of claim 14, wherein said base includes a pair of upwardly extending legs which are spaced to define a space for receiving said adaptor body, said legs each having a detent on an upper end of said leg which extends inwardly into said space, said adaptor body having a groove on its exterior which is adapted to receive said detents, the spacing and location of said detents in relation to the diameter of said groove being such that the tubular body may be manually pressed into said space and said detents cooperate with said groove to hold the tubular body in position on said base.

16. An apparatus for removably connecting a fluid supplied tube to an intravenous catheter, said apparatus comprising:
an adaptor having a body having a forward end configured to engage an end of the catheter and a rear end configured to received an end of the fluid supply tube, said body having longitudinal axis; and
an auxiliary connector mounted on said adaptor for securing said engagement between said forward end and said catheter end, said auxiliary connector comprising:
a support arm mounted on said adaptor;
a clip support element mounted on said support arm, said support arm being fixedly mounted to said clip support element generally transverse to a clip, said clip comprising a forward latch configured to engage the catheter end, said clip being mounted on said clip support element so as to be movable thereon such that said latch engages the catheter end, said support arm being relatively more flexible than said clip support element such that pressure applied to said auxiliary connector causes said support arm to flex, whereby said latch is moved outwardly away from the catheter connector in order to disconnect said adaptor from the catheter end.

17. The apparatus of claim 16 additionally comprising a flexible anchor pad having an self-adhesive backing, said anchor pad supporting an adaptor base comprising a pair of upstanding projections spaced apart to receive said adaptor.

18. The apparatus of claim 16, wherein said forward end of said adaptor is configured to engage a luer-type connector disposed on the catheter end.

19. The apparatus of claim 16, wherein said forward end of said adaptor is configured to engage a septum connector disposed on the catheter end.

20. The apparatus of claim 19, wherein said adaptor comprises a tubular body defined between said forward end and said rearward end, said forward end comprising a needle cantilevering from said tubular body and being in fluidic communication with said tubular body, said forward end further comprising a shield disposed about said needle.

21. The apparatus of claim 16 additionally comprising a base for mounting on a patient's skin, said base having a pair of upstanding legs spaced apart to receive said adaptor, said base legs having detents which fit within an annular groove on said adaptor to permit rotation of said adaptor about a longitudinal axis of said adaptor while remaining captured on said base.

22. The apparatus of claim 16, wherein said adaptor additionally comprises an interengaging element disposed between said clip support element and said clip to hold said clip in a manually selected positioned on said clip support element.

23. The apparatus of claim 22, wherein said interengaging element comprises a plurality of ratchet teeth and a pawl which cooperates with said teeth to hold said clip in said selected position.

24. An apparatus for removably interconnecting a fluid supply tube to an intravenous catheter, said apparatus comprising:
an adaptor having a body having a forward end configured to engage an end of the catheter and a rear end configured to engage an end of the fluid supply tube, said body having longitudinal axis; and
an auxiliary connector mounted on said adaptor for securing said engagement between said forward end and a catheter end, said auxiliary connector comprising:
a support arm mounted on said adaptor, said support arm having a width measured in a direction generally parallel to said longitudinal axis of said adaptor; and
a clip element comprising a forward latch configured to engage the catheter end, said latch being coupled to said support arm so as to move with respect thereto such that the latch engages the catheter end, said clip element having a thickness measured in a direction generally normal to said longitudinal axis, said thickness of said clip element being larger than said width of said support arm such that said support arm is relatively more flexible than said clip element, whereby pressure applied to said auxiliary connector causes said support arm to flex to move said latch outwardly from the catheter connector in order to disconnect said adaptor from the catheter end.

25. A method of connecting a fluid supply tubing to a catheter comprising the steps of:
inserting a forward end of an adaptor into a rear end of a catheter;
engaging the catheter end with a clip which is slidably mounted on said adaptor;
sliding said clip rearwardly on said adaptor to grip the catheter end in a gripping position;
locking said clip to maintain said clip in said gripping position by means of interengaging structure; and
disconnecting said adaptor from the catheter end by deflecting a support arm supporting said clip such that a forward end of said clip is moved outwardly away from the catheter end.

26. A method of supporting and facilitating the changing of tubing connected to a catheter, comprising:
inserting a needle of a forward end of a tubular adaptor body into a septum of a catheter end having a tapering exterior decreasing in diameter in a direction remote from said adaptor, and connecting the rear end of the adaptor to a supply tubing;
engaging said septum with a slidably latch mounted on said adaptor;
sliding said latch towards said septum to- grip the catheter septum in a gripping position; and
locking said latch in said gripping position by interengaging structure on said latch and adaptor.

27. The method of claim 26, additionally comprising the steps of:
providing said latch comprising a clip having a forward latching portion engaging said catheter septum and a rear portion slidably mounting on said adaptor; and
depressing said clip rear portion about a support element on said adaptor to raise said clip forward end to release said latching portion from said catheter septum.

28. The method of claim 26, additionally comprising the steps of:
mounting said adaptor body in a base;
attaching said base to the patient's skin; and
rotating the adaptor body from a high profile position wherein said latch extends upwardly to a low profile position wherein said latch structure lies close to the patient's skin.

* * * * *